Figure 1A:
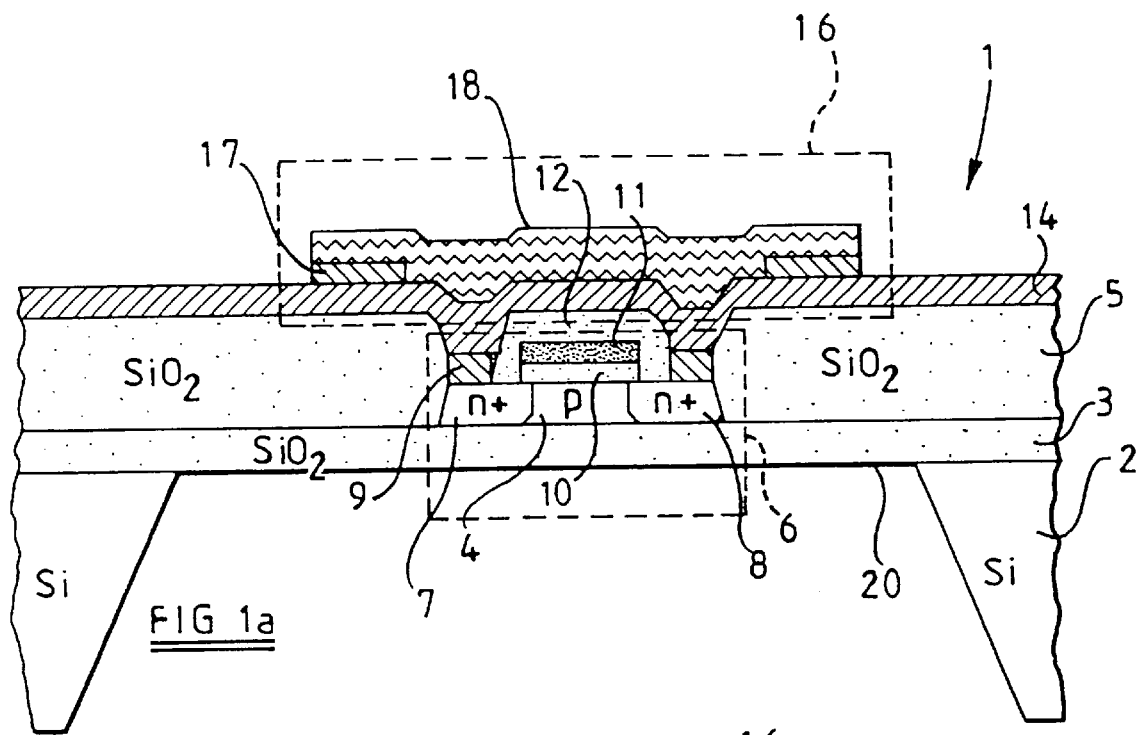

United States Patent [19]
Gardner et al.

[11] Patent Number: 6,111,280
[45] Date of Patent: Aug. 29, 2000

[54] GAS-SENSING SEMICONDUCTOR DEVICES

[75] Inventors: Julian Gardner, Coventry; Florin Udrea, Cambridge, both of United Kingdom

[73] Assignee: University of Warwick, Coventry, United Kingdom

[21] Appl. No.: 09/341,794
[22] PCT Filed: Jan. 13, 1998
[86] PCT No.: PCT/GB98/00100
§ 371 Date: Sep. 14, 1999
§ 102(e) Date: Sep. 14, 1999
[87] PCT Pub. No.: WO98/32009
PCT Pub. Date: Jul. 23, 1998

[30] Foreign Application Priority Data

Jan. 15, 1997 [GB] United Kingdom ............... 9700723

[51] Int. Cl.[7] .................................................. H01L 29/72
[52] U.S. Cl. .................... 257/253; 257/347; 257/401; 257/414
[58] Field of Search .................... 257/253, 401, 257/414, 347

[56] References Cited

U.S. PATENT DOCUMENTS

| 4,502,938 | 3/1985 | Covington et al. | 257/253 |
| 4,878,015 | 10/1989 | Schmidt et al. | 324/71.5 |

FOREIGN PATENT DOCUMENTS

| 0192488 | 8/1986 | European Pat. Off. |
| 2195208 | 3/1988 | United Kingdom . |
| 9519563 | 7/1995 | WIPO . |

OTHER PUBLICATIONS

S. Wessel, et al.; Microelectronics Journal, 23, 1992, 451–456, "A CMOS Thermally–Isolated Heater Structure as a Substrate for Semiconductor Gas Sensors".

Search Report for Application No. GB 9700723.1; Dated Mar. 20, 1997.

Primary Examiner—Edward Wojiechowicz
Attorney, Agent, or Firm—Renner, Otto, Boisselle & Sklar LLP

[57] ABSTRACT

A gas-sensing semiconductor device 1 is fabricated on a silicon substrate 2 having a thin silicon oxide insulating layer 3 on one side and a thin silicon layer 4 on top of the insulating layer 3 using CMOS SOI technology. The silicon layer 4 may be in the form of an island surrounded by a silicon oxide insulating barrier layer 4 formed by the known LOCOS oxidation technique, although other lateral isolation techniques may also be used. The device 1 includes at least one sensing area provided with a gas-sensitive layer 18, a MOSFET heater 6 for heating the gas-sensitive layer 18 to promote gas reaction with the gas-sensitive layer 18 and a sensor 16, which may be in the form of a chemoresistor, for providing an electrical output indicative of gas reaction with the gas-sensitive layer 18. As one of the final fabrication steps, the substrate 2 is back-etched so as to form a thin membrane 20 in the sensing area. Such a device can be produced at low cost using conventional CMOS SOI technology.

20 Claims, 8 Drawing Sheets

- □ Silicon
- ▨ Oxide
- ▨ Polysilicon
- ▨ Sensitive layer
- ▨ Metal
- ▨ Passivation layer

- ☐ Silicon
- ⋯ Oxide
- ▒ Polysilicon
- ∿ Sensitive layer
- ▨ Metal
- ▩ Passivation layer
- ▦ Porous metal

- ☐ Silicon
- ▨ Oxide
- ▦ Polysilicon
- 〰 Sensitive layer
- ▧ Metal
- ▩ Passivation layer
- ▦ Porous metal ☐ Silicon
▦ Oxide
▓ Polysilicon
∿ Sensitive
▨ Metal
▧ Passivation layer
▦ Porous metal

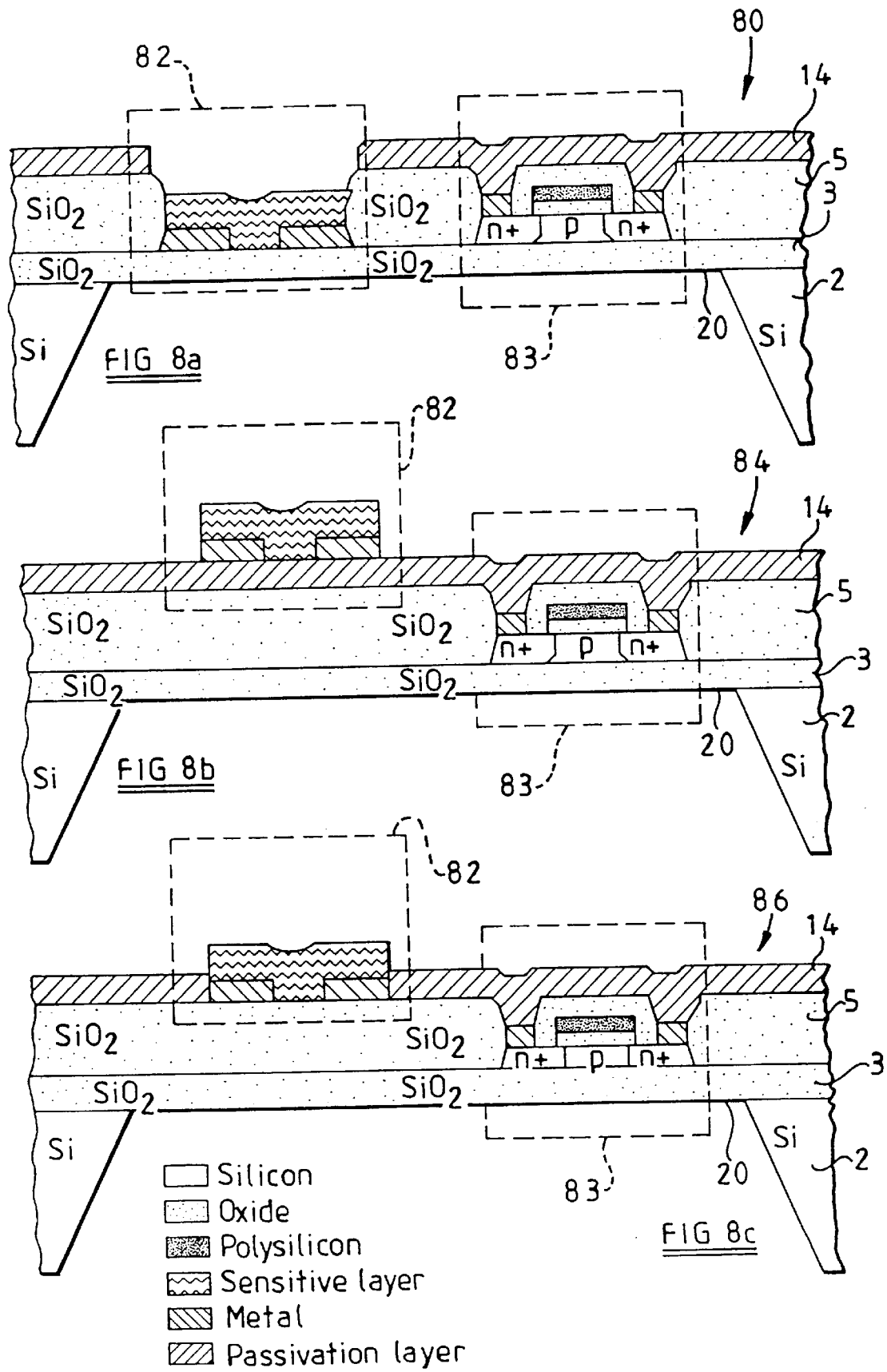

GAS-SENSING SEMICONDUCTOR DEVICES

This invention relates to gas-sensing semiconductor devices for detecting the presence and/or concentration of one or more gases.

It is known to fabricate a gas microsensor within a semiconductor device. In particular it is known to produce high-temperature metal oxide conductimetric sensors using alumina substrates and semi-manual production methods. Recently attempts have been made to manufacture silicon versions of such sensors employing a platinum heater integrated with a thin insulating membrane of oxide or nitride. Such sensors offer a lower power consumption than conventional sensors when operating at 300° C. to 600° C. However the two part deposition of the membrane of such a sensor and the deposition of the metal heater layer sandwiched between the two membrane layers makes the fabrication process incompatible with integrated circuit technology. There has also been much interest in the development of MOSFET potentiometric sensors using catalytic gates, for example of palladium which run at temperatures of between 120° C. and 200° C. However such sensors will have limited application due to their inefficiency and relatively high cost.

It is an object of the invention to provide an improved gas-sensing semiconductor device which can be produced at low cost using conventional bulk fabrication processes.

According to the present invention there is provided a gas-sensing semiconductor device as defined by the accompanying claims.

Such a gas-sensing semiconductor device can be produced so as to have very low power consumption using a series of fabrication steps compatible with known CMOS SOI (silicon on insulator) technology for integrated circuits. As compared with conventional planar integrated gas sensors, this considerably simplifies the fabrication of the device, and thus decreases the manufacturing cost. Furthermore the device may be integrated with processing circuitry, such as a processor unit and a driving circuit, on a single chip so as to produce a "smart" gas microsensor. Unlike in conventional gas microsensors, the heater can be produced without requiring any fabrication steps in addition to those already employed in the IC processing. The use of SOI technology also allows accurate bipolar temperature sensors to be integrated into the device.

SOI technology is commonly based on wafer bonding or implantation of oxygen deep into the substrate followed by epitaxial growth (known as SIMOX techniques). CMOS SOI integrated circuits may be fabricated by forming a thin layer of insulating material, such as silicon oxide, on the semiconductor substrate followed by forming of a thin silicon layer on top of the insulating layer. Other insulating materials can be used in place of silicon oxide, such as silicon nitride or a combination of silicon oxide and silicon nitride. Individual semiconductor devices, such as MOSFET's, are then fabricated within the thin silicon layer using known fabrication steps. Because the devices are formed within a very thin silicon/insulator membrane, of 0.2 $\mu$m thickness or example, SOI technology results in high speed/low power CMOS performance, as ell as providing simple and efficient device isolation, reduced parasitic capacitances, latch-up elimination and reduced short-channel effects. In addition fully depleted devices (with an ultra-thin SOI layer) have been reported to have attractive features. They do not exhibit kink phenomena, have a sharp sub-threshold slope, and are stable in terms of dynamic floating body effects relating to impact-ionisation and charge-pumping phenomena The SOI transistors also possess a lower off-state leakage current by a factor of about 10–100 when compared with conventional bulk silicon devices. This is important in reducing the stand-by power dissipation. In addition SOI technology enables device operation at higher temperatures than conventional devices, mainly due to reduced leakage currents.

This allows very high temperatures in the membrane area (up to 600° C. for some sensing materials to react with the gases) and relatively high temperatures in the neighbouring circuit area (up to 250° C.) without being affected by high leakage currents or latch-up as in the case of conventional bulk CMOS processes. Therefore SOI technology is very well suited for smart gas sensors.

In the gas-sensing semiconductor device of the invention the sensing area comprises a membrane formed by the thin insulating layer and the top thin semiconductor layer after removal of the substrate material, for example using a standard anisotropic back-etching process. The thin insulating layer, of silicon oxide for example, which is part of the standard SOI structure, serves a dual purpose, namely (i) it acts as an etch stop in the sensing area and thermally isolates the sensing area so as to reduce power losses at high temperatures, and (ii) it provides high grade electrical isolation from any associated integrated circuit area, incorporating transducer and associated processing circuitry for example, as well as providing reduced interferences, latch-up elimination and reduced capacitances in the specific case of low power CMOS SOI integrated circuits.

Due to the high thermal isolation properties of the membrane, high temperatures can be developed with very low electrical power consumption, and this is particularly advantageous in applications in which high temperatures are required for the gas to react with the active material of the gas-sensitive layer. The nature and concentration of different gases or of a mixture of gases can be determined by measuring the change in conductivity of the gas-sensitive layer at different temperatures. Organic and catalytic gas-sensitive layers may react at low temperatures (less than 100° C.) or medium temperatures (100° C. to 200° C.) whereas metal oxide gas-sensitive layers may require temperatures in excess of 200° C. Thus a gas microsensor array device can be built by integrating several individual sensor cells utilising different gas-sensitive layers in the same chip. The individual sensor cells can be built on the same membrane or can have separate membranes. Such a microsensor array device possesses the advantages over individual sensors of improved gas selectivity, lower noise and reduced effect of poisoning through superior structural design or signal processing.

Figure 1B:
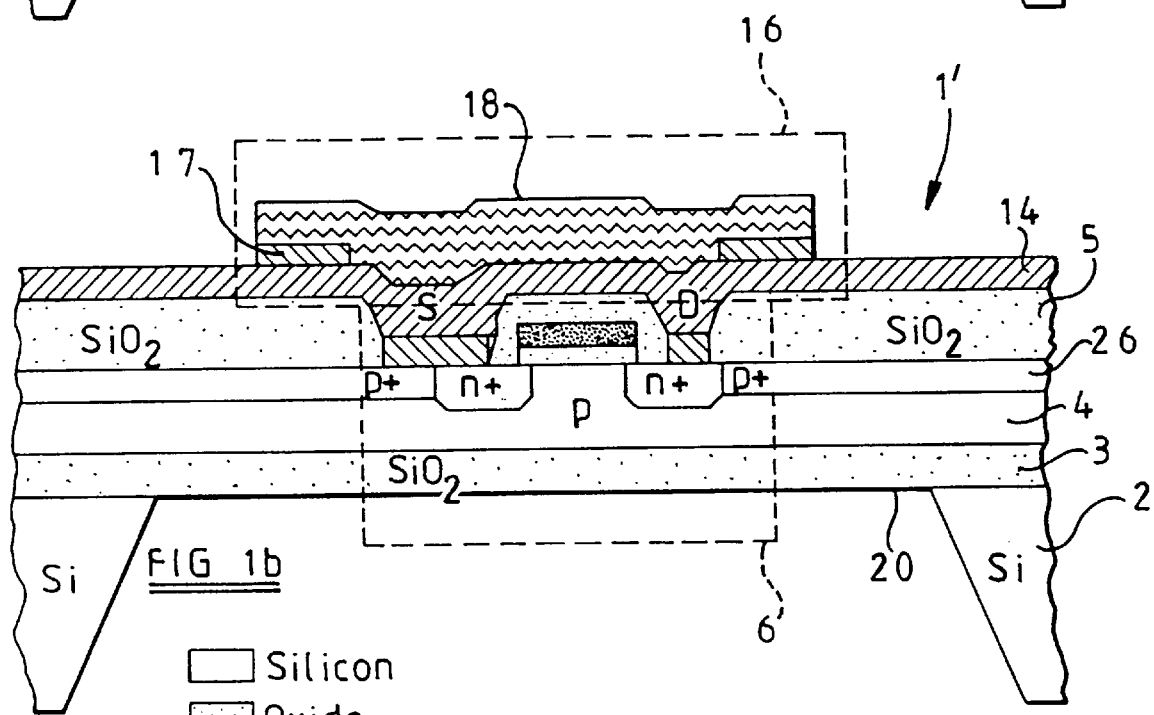
Figure 2:
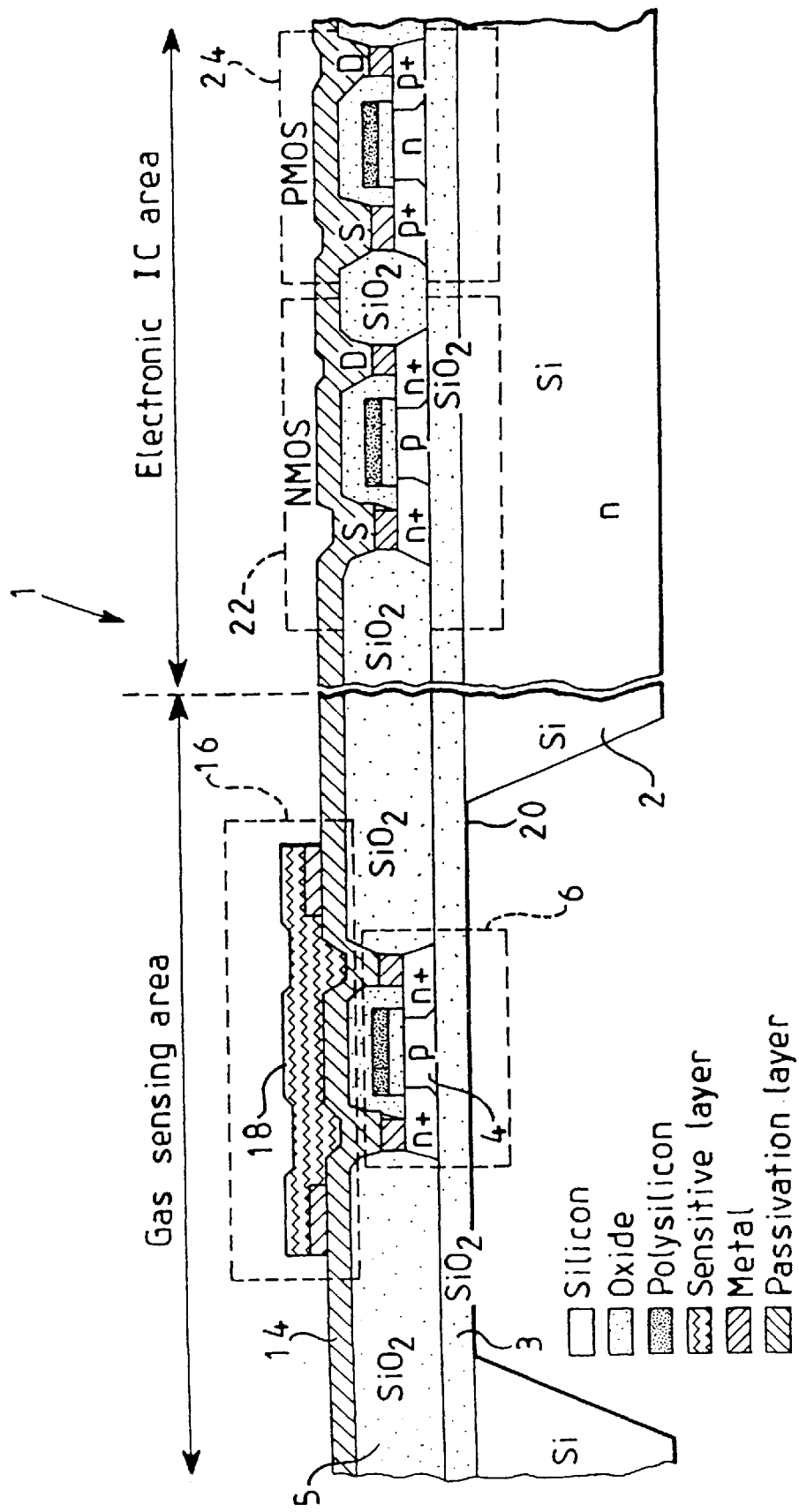
Figure 3:
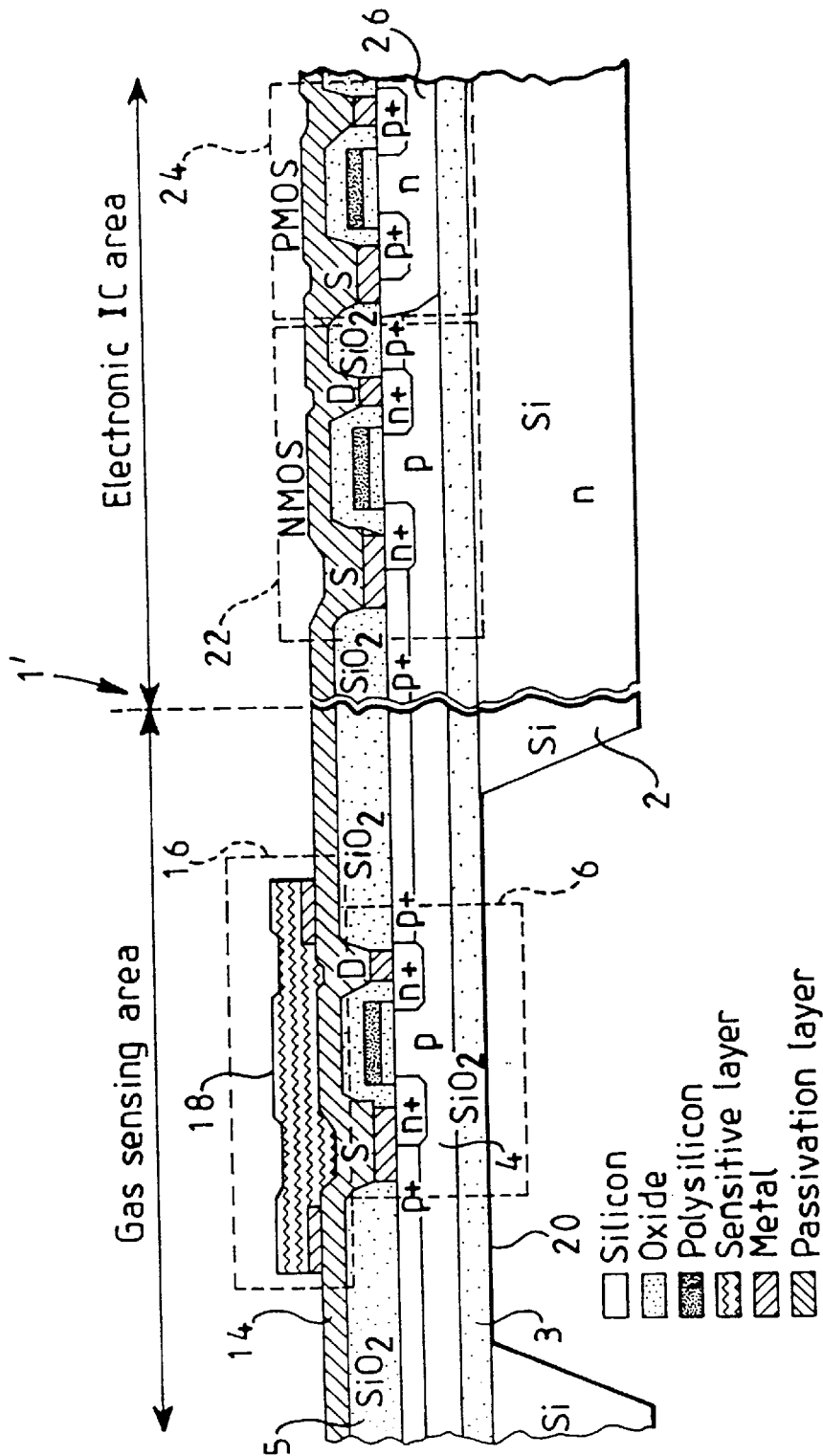

In order that the invention may be more fully understood, a number of embodiments of the invention will now be described, by way of example, with reference to the accompanying drawings, in which:

FIGS. 1a and 1b show sections through a sensing area of two alternative embodiments of the invention;

FIGS. 2 and 3 show sections through the sensing area and the IC area of the embodiments of FIGS. 1a and 1b; and FIGS. 4a, 4b, 5a, 5b, 6a, 6b, 7a, 7b, 8a, 8b and 8c are sections through the sensing areas of a number of other embodiments of the invention.

The embodiments of gas-sensing semiconductor device in accordance with the invention to be described with reference to the drawings are fabricated utilising CMOS SOI technology so as to provide gas sensing areas integrated with IC circuitry in a single chip, each sensing area being a thin membrane formed by a thin insulating layer and a thin semiconductor layer. Unless specified the structures in these embodiments can operate at temperatures up to 600° C. in the sensing area. The thin insulating layer, which provides thermal isolation, may be an oxide, a nitride, a combination of oxide and nitride or some other insulating material. Unlike in conventional gas microsensors, there is no need for special low-stress membrane deposition involving an expensive and difficult fabrication process. Particular attention is drawn in the accompanying description to the fabrication of the device in the sensing areas, although it will be understood that IC fabrication will be effected simultaneously to provide the associated circuitry in other areas of the device.

In the embodiment of FIG. 1a the device 1 is fabricated on a silicon substrate 2 having a thin silicon oxide insulating layer 3 on one side, and a thin silicon layer 4 on top of the insulating layer 3. In this embodiment the silicon layer 4 is in the form of an island surrounded by a silicon oxide insulating barrier layer 5 formed by the known LOCOS oxidation technique so as to extend vertically to substantially meet the thin insulating layer 3. The LOCOS oxidation technique has the advantage of producing both efficient lateral electrical isolation in the sensing area and the associated electronic IC areas, and also thermally insulating the sensing area The thermal oxide has a much lower thermal conductivity than the silicon and therefore the thermal power losses in the sensing area will be greatly reduced. Other lateral isolation techniques, such as MESA etching of the thin silicon layer, trench isolation (trenches filled with oxide or other insulating material) or SIMOX TDI (separation by implanted oxygen to provide total dielectric isolation), may also be used in a similar way.

Furthermore a MOSFET heater 6, is formed in the sensing area by known CMOS SOI or Bi-CMOS SOI processing and comprises a n+ source layer 7 and a n+ drain layer 8 diffused in the lowly doped p-type silicon layer 4. Although the heater 6 is shown as an n-type MOSFET, it will be appreciated that a p-type MOSFET heater could also be employed. A silicon oxide layer 10 is grown at the surface to form the gate oxide followed by the deposition and patterning of a polysilicon layer 11 on top of the gate oxide. The n+ source layer 7 and n+ drain layer 8 are further implanted and could be self-aligned to the gate and LOCOS barrier layer 5. A metalisation layer 9 is applied and patterned on top of the source and drain diffusions. The pads for the source, drain and gate contacts (not shown) are placed outside the membrane area to avoid thermal and mechanical stress. Furthermore a further silicon oxide layer 12 is applied to the gate, and a passivation layer 14 is deposited in a manner compatible with conventional SOI technology. The passivation layer 14 may be an oxide and/or nitride layer or a thin glass layer, although other passivation layers, such as amorphous materials and polyimide, are possible. The same processing steps are used to fabricate the low power transistors in the electronic IC areas.

In addition to the MOSFET heater 6, a chemoresistor sensor 16 is fabricated in the sensing area by depositing a metallisation layer 17 on top of the passivation layer 14 to form two spaced electrodes and by subsequently placing a gas-sensitive layer 18 made either of an inorganic material (such as tin oxide) or an organic material (such as a polymer or pthalocyanine) so as to span the two electrodes. The gas-sensitive layer 18 can be deposited by sputtering etc. or can be electrochemically grown onto the two electrodes (as in the case of conducting polymers). As one of the final steps in the fabrication process the substrate 2 is back-etched so as to form the thin membrane 20 in the sensing area, with the insulating layer 3 serving to stop the back-etching.

Either a single chemoresistor sensor 16 or an array of chemoresistors may be provided on top of the heater 6, the or each chemoresistor comprising a layer of inorganic or organic material. In a different design the chemoresistor can be disposed laterally and surrounded by the MOSFET heater.

When a positive potential with respect to the source is applied to the gate of the MOSFET heater 6, an inversion layer channel is formed under the insulated gate and a current (electron) flows through the channel. Due to the high thermal insulation in the sensing area and very low thermal capacitances, the sensing area heats up rapidly, thus allowing gas molecules to react with the gas-sensitive layer 18 of the sensor 16. The temperature is controlled by the gate potential of the MOSFET heater 6. The source terminal is typically connected to ground while the drain potential is typically in the range of 1V to 5V. The p-type silicon layer 4 may be left floating or connected to the source. When the gas interacts with the gas-sensitive layer 18, the conductivity of the gas-sensitive layer 18 changes, and the resulting changing current can be detected by appropriate detection circuitry (not shown).

In order to monitor the temperature in the sensing area, a CMOS or Bi-CMOS integrated temperature sensor (not shown) can be fabricated in the sensing area adjacent to the gas-sensitive layer 18. Such a temperature sensor may comprise unipolar or bipolar devices formed by SOI technology and may make use of variation of the emitter-base voltage with temperature. Such temperature sensors are widely used and give accurate results.

The MOSFET heater 6 may have an interdigitated structure to uniformly heat the sensing area, and there is no need for deposition of special metal layers, of platinum or NiFe for example, to form a conventional metallic heater resistor. If the sensor comprises an array of individual sensor cells, a single common heater may be used for all the sensor cells, or alternatively an array of MOSFET heaters may be employed. If required, such a heater array could be adapted to heat different sensor cells to different temperatures, in which case the source diffusion could be common to all the heaters (or the sources of all the heaters could be connected together by a metal layer) and connected to a fixed voltage, such as ground for example. Similarly the drain diffusion could be common to all the heaters (or the drains of all the heaters could be connected together by a metal layer) and connected to a fixed potential, such as 3V for example. The gate terminals of the heaters must remain separate, however, so that, by applying different voltages to the gates of the heaters, different power levels can be established and thus different temperatures can be developed across the sensing area. A desired temperature gradient or temperature pattern, that is an uneven temperature distribution, can also be developed across part of the sensing area by controlling the channel length of a MOSFET heater. At given drain, source and gate potentials, a longer channel length results in a lower channel current and thus in less power being dissipated.

The use of MOSFET heaters also drastically simplifies the driving circuitry since, because of the high input impedance of the gate, a MOSFET heater can be controlled by digital circuits or operational amplifiers. Temperature cycles can be applied across the sensing area by driving the MOSFET heaters with digital or analogue switching devices. Furthermore, if required, the gas-sensitive layer could be cleaned to remove gas impurities by applying a voltage higher than the normal operating voltage to the gate of the or each heater in a clean atmosphere, so as to cause any contaminating compounds to be driven out of the gas-sensitive layer by the very high temperatures developed.

FIG. 2 shows the sensing area of FIG. 1 a together with an associated electronic IC area of the same device 1, and shows in particular the fabrication of an n-type MOSFET 22 and a p-type MOSFET 24 formed in the IC area of the substrate by the same processing steps to those used in the fabrication of the sensing area as described above, with reference to FIG. 1(a).

FIG. 1b shows a variation of the structure of FIG. 1a in which a device 1' comprises a similar thin insulating layer 3 and silicon layer 4 on a substrate 2, as in FIG. 1a except that the silicon layer 4 is not fully depleted during on-state operation of the MOSFET, so that the silicon layer 4 is thicker than in the previous case. This is known as non-fully depleted CMOS SOI technology. Lateral isolation (not shown) can employ, for example, junction isolation structure, trench oxidation, MESA etching or, for relatively thinner silicon layers, LOCOS oxidation. A p+ layer 26 is provided to avoid parasitic conduction between individual cells of the device. FIG. 3 shows the sensing area of such a device, together with an associated electronic IC area formed by the same processing steps.

Alternatively the sensor may be formed by a MOSFET having a gate formed by the gas-sensitive layer and a thin gate oxide, as described more fully below. In this case the gas-sensitive layer may be made of organic material, such as a conductive polymer, or inorganic conductive material, such as a metal oxide. When the gas reacts with the gas-sensitive layer, the work function of the gas-sensitive layer changes, thereby modifying the threshold voltage and the transfer and output characteristics of the MOSFET.

In the further embodiments to be described below, the same reference numerals will be used as in FIGS. 1a, 1b, 2 and 3 to denote corresponding features. In the device 40 of FIG. 4a, the MOSFET heater 42 is also used as the sensing element, and incorporates a gas-sensitive layer 43 which is applied to the gate on top of the silicon oxide layer 10. The gas-sensitive layer 43 may be made of an organic conductive or semiconducting material, such as a conjugated polymer, or an inorganic semiconducting material, such as a catalytically doped metal oxide. When the gas reacts with the gas-sensitive layer 43, the work function of the gas-sensitive layer 43 changes, thereby modifying the threshold voltage of the MOSFET. Thus the nature of the gas detected and/or its concentration can be determined by monitoring the change in the channel threshold current or sub-threshold current in the presence of the gas, by comparison of the I-V characteristics in the presence of the gas with the I-V characteristics in the absence of the gas, or by directly detecting the threshold voltage. This particular structure can be used for relatively low temperatures (below 100 C.) and the temperature can be adjusted by varying the drain-source voltage.

Figure 4A:
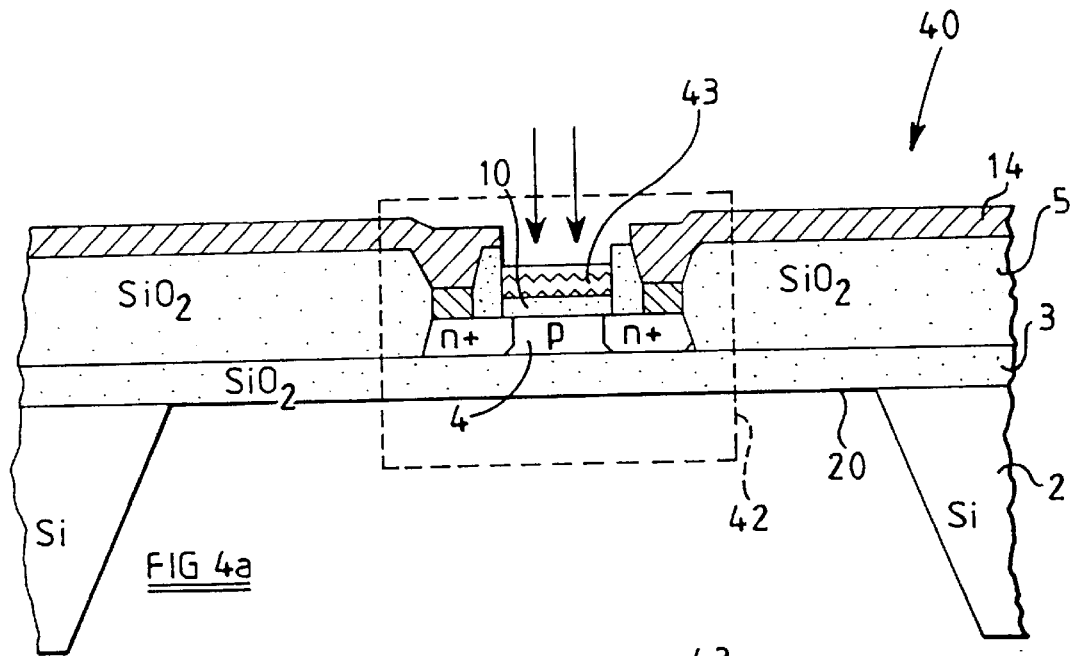
Figure 4B:
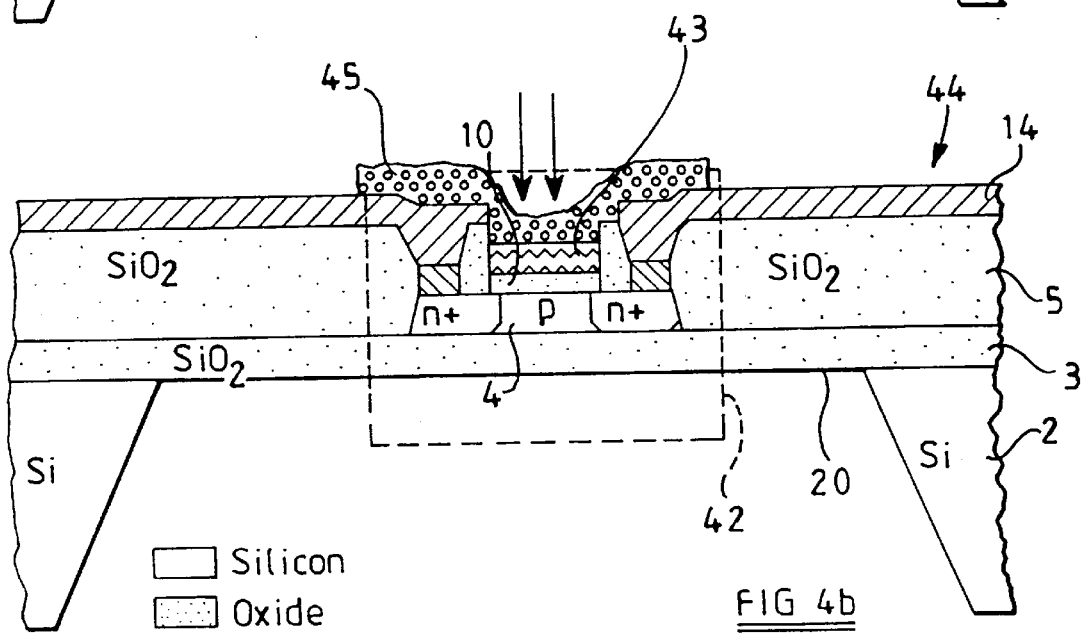

The device 44 of FIG. 4b is a variation of the device 40 of FIG. 4a in which a porous metal layer 45, made of gold for example, is deposited on top of the gas-sensitive layer 43 to form a controllable gate. The porous metal layer 45 allows the gas to diffuse through to the gas-sensitive layer 43. By applying a potential to the gate, and provided that the drain potential is higher than the source potential, a current is established in the MOSFET and power is dissipated in the sensing area. Thus the MOSFET acts as a heater with the desired temperature being set by the drain and gate potentials so that the heater is controllable in a similar manner to the heater of FIG. 1a, except that the MOSFET also constitutes the sensing element in FIG. 4b. When gas reacts with the gas-sensitive layer 43, the work function of the gas-sensitive layer 43 changes and therefore the threshold voltage of the MOSFET changes. Since the gate voltage is much higher than the change in the threshold voltage, this will not significantly affect the power dissipated, and thus the temperature. However, the change in the current or voltage due to the variation of the work function in the presence of the gas at a given temperature, that is at a given MOSFET bias point, can be detected by a highly accurate integrated CMOS or Bi-CMOS transducer.

In a non-illustrated variation of the device FIG. 4b, the porous layer is also the gas-sensitive layer, being made of a thin film of catalytic metal, such as palladium or iridium for example. However, such a catalytic metal film could not be produced by standard CMOS technology and would need to be sputtered down as a final process or via lift-off.

Figure 5A:
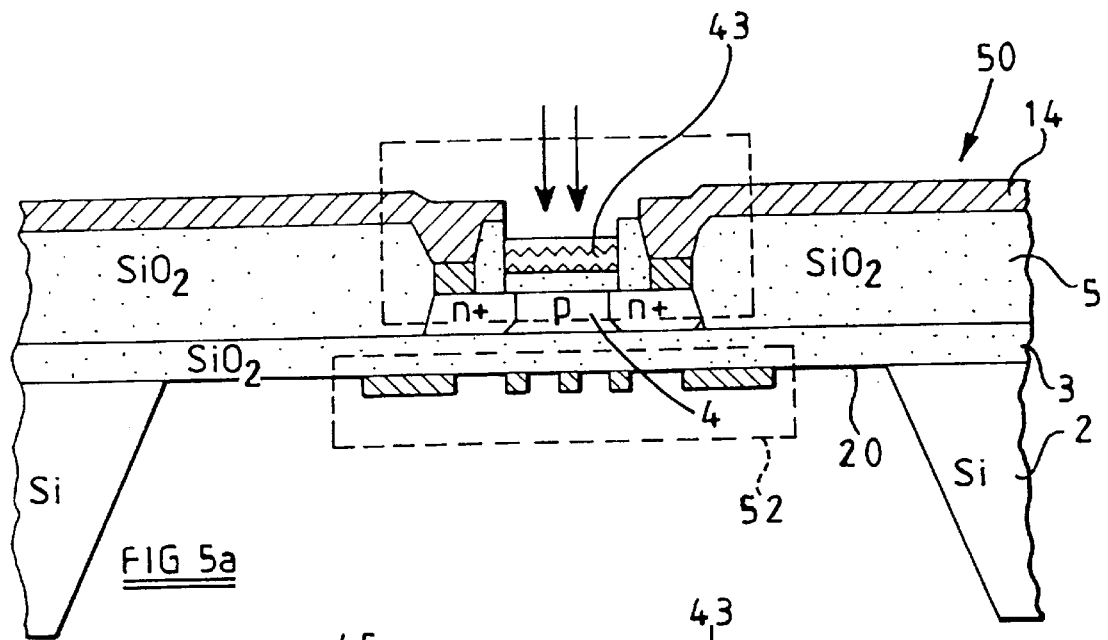
Figure 5B:
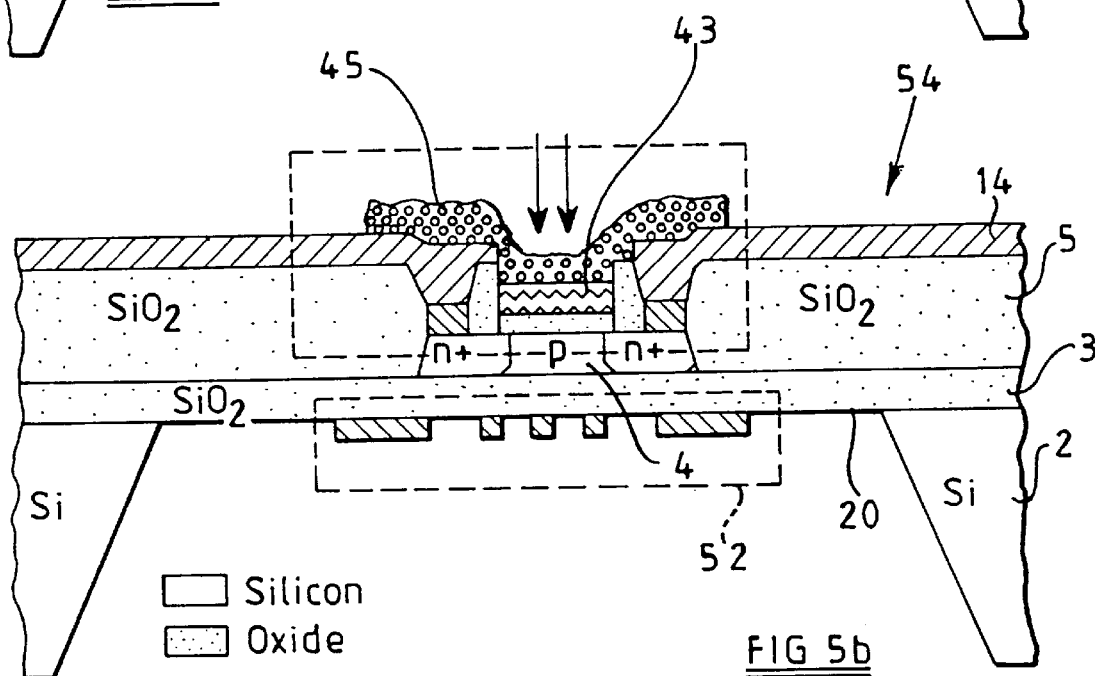

FIGS. 5a and 5b show variations 50 and 54 of the structures of FIGS. 4a and 4b respectively in which an additional heater is provided by a heater resistor 52 in the form of a resistive layer, of platinum or NiFe for example, deposited on the back side of the membrane 20 and connected to two electrodes. The structure can be heated up by applying a voltage drop across the heater resistor 52, and the temperature can be monitored by detecting the change of the heater resistance with current.

Figure 6A:
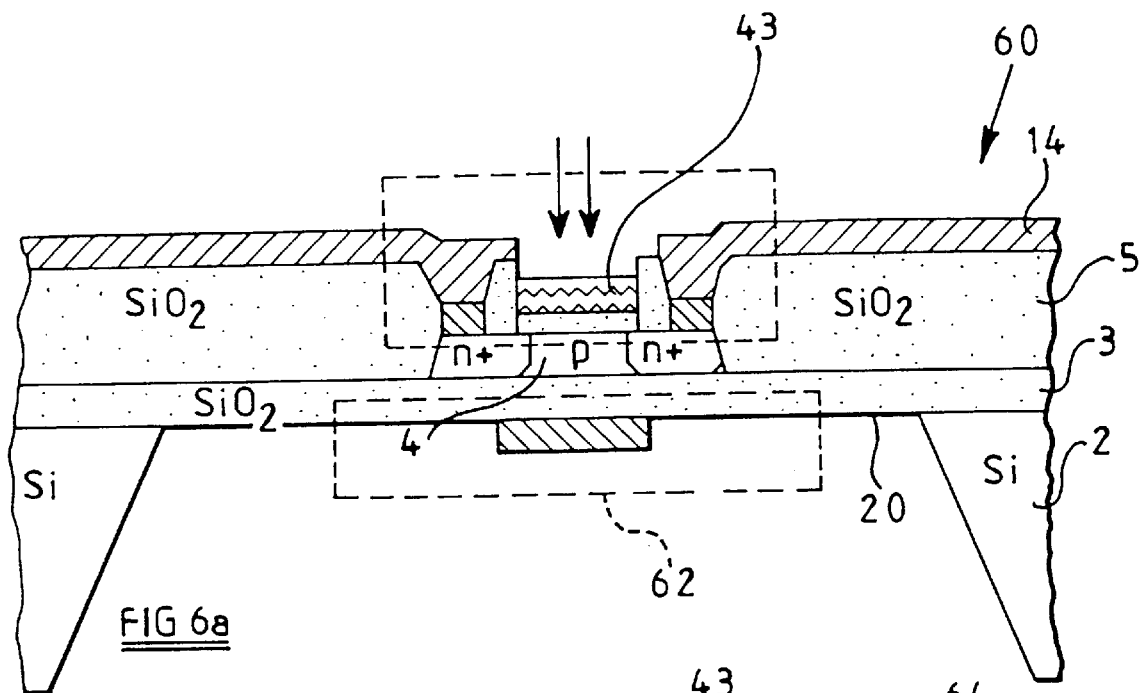
Figure 6B:
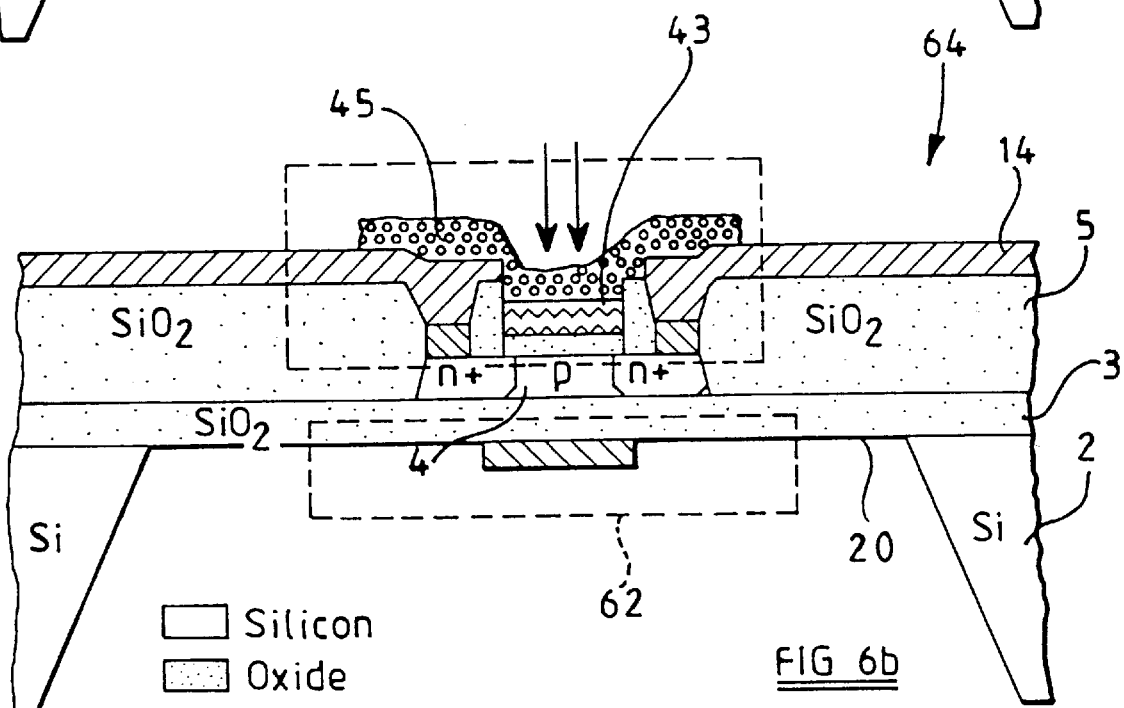

FIGS. 6a and 6b show variations 60 and 64 of the structures of FIGS. 4a and 4b respectively in which a metal gate electrode 62 is deposited on the back side of the membrane 20 after back-etching, in order to control the heater current flowing through the back side of the MOSFET. Thus the structures of FIGS. 6a and 6b can be considered as incorporating a back-side MOSFET heater. This is only possible when the source and drain diffusions reach the thin insulating layer 3. In the case of a n-channel MOSFET, when a positive voltage is applied to the back-gate electrode 62, a back channel is formed between the source and the drain at the interface between the thin insulating layer 3 and the silicon layer 4. The sensing MOSFET operates in parallel with the back-side heater MOSFET so that there are two MOSFET channel paths from source to drain arranged in parallel. In the structure of FIG. 6b, both the sensing/heater MOSFET and the back heater MOSFET participate in heating, and therefore the temperature is controlled by the voltage applied to the two parallel gates.

Figure 7A:
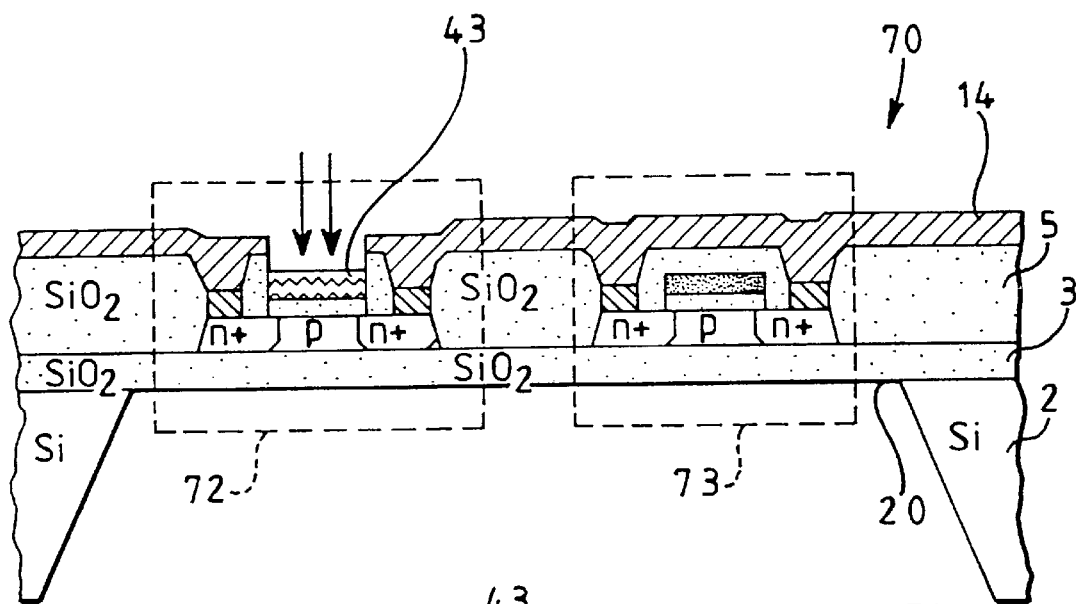
Figure 7B:
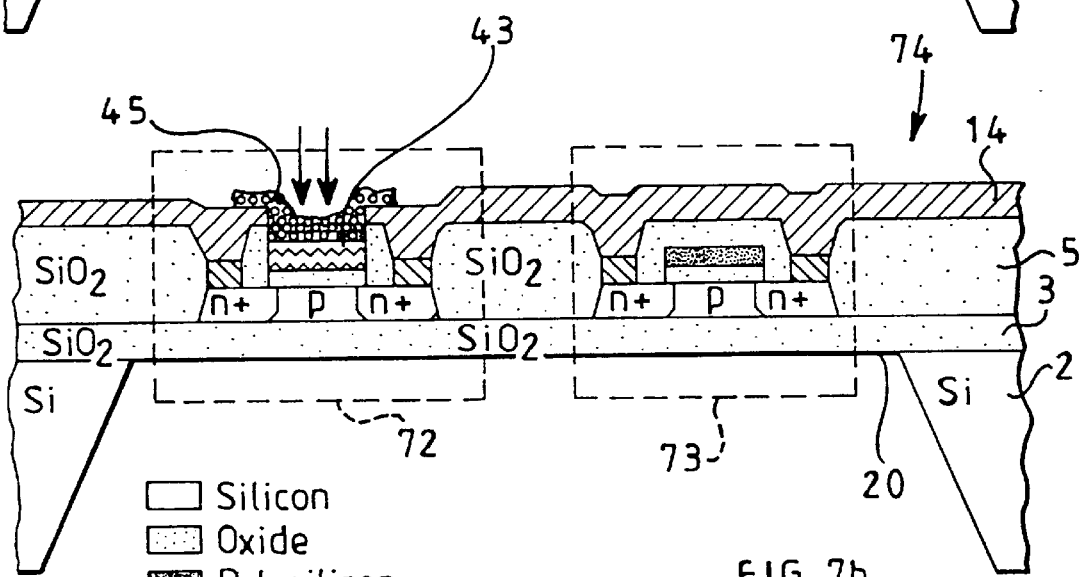

FIGS. 7a and 7b show further variations 70 and 74 in which a sensing MOSFET 72 and heater MOSFET 73 are disposed laterally adjacent one another in the sensing area. Several sensing MOSFET's can be used to form a sensor array, and the layout design may consist of alternate sensing MOSFET's and heater MOSFET's. Alternatively sensing MOSFET's may be alternated with conventional heaters.

FIGS. 8a, 8b and 8c show variations 80, 84 and 86 in which a chemoresistor sensor 82 and a heater MOSFET 83 are disposed laterally adjacent one another in the sensing area. The chemoresistor sensor 82 can be formed on the thin insulating layer 3 (FIG. 8a), on the passivation layer 14 (FIG. 8b) or on the silicon barrier layer 5 (FIG. 8c).

The above structures (except device 40 in FIG. 4a) can operate at very high temperatures of up to 600° C.

The above structures can also be used as microcalorimeters (or as both chemoresistors and microcalorimeters) in which the additional heat liberated or absorbed by the gas-sensitive layer in the presence of the gas is detected. In this case the temperature of the sensing material changes as a result of its reaction with the gas so that the nature of the gas and/or its concentration can be determined by monitoring the heat liberated or absorbed by the gas-sensitive layer in the presence of the gas. An appropriate gas-sensitive layer for such an application would be a non-electrically conducting material such as gamma-alumina (pellistor). Chemoresistive materials such as tin oxide change their thermal conductivity so that it is possible to monitor the change in thermal conductivity, the heat liberated and the change in the electrical conductivity at high temperatures. This is an attractive technique in SOI MOSFET devices because of the very fast thermal response permitting rapid measurements.

What is claimed is:

1. A gas-sensing semiconductor device comprising a semiconductor substrate (2), a thin insulating layer (3) on one side of the substrate, and a thin semiconductor layer (4) on top of the thin insulating layer, wherein the device includes at least one sensing area in which the material of the substrate has been removed to leave a membrane (20) formed by the thin insulating layer and the thin semiconductor layer, and wherein the at least one sensing area is provided with a gas-sensitive layer (18, 43) and a heater (6, 42, 52, 62, 73, 83) for heating the gas-sensitive layer to promote gas reaction with the gas-sensitive layer, and a sensor (16, 42, 72, 82) for providing an electrical output indicative of gas reaction with the gas-sensitive layer, characterised in that the at least one sensing area incorporates a MOSFET formed in the thin semiconductor layer (4) and forming part of the heater and/or sensor.

2. A device according to claim 1, wherein the heater (6, 42, 52, 62, 73, 83) incorporates said MOSFET in the vicinity of the gas-sensitive layer (18, 43).

3. A device according to claim 1, wherein the gas-sensitive layer (18, 43) is incorporated in the gate of said MOSFET so that the threshold of the MOSFET changes in response to gas reaction with the gas-sensitive layer.

4. A device according to claim 3, wherein the gate comprises a conductive polymer layer which acts as the gas-sensitive layer.

5. A device according to claim 1, wherein a gate electrode (62) is applied to the back side of the thin insulating layer (3) in order to control a heating current in said MOSFET.

6. A device according to claim 1, wherein a gas-permeable metal layer (45) is applied on top of the gas-sensitive layer (18, 43) to allow gas to diffuse through the gas-permeable metal layer towards the gas-sensitive layer.

7. A device according to claim 1, wherein the sensor (16, 42, 72, 82) incorporates at least said MOSFET in the vicinity of the gas-sensitive layer (18, 43).

8. A device according to claim 1, which has been produced utilising CMOS SOI or bi-CMOS SOI fabrication steps.

9. A device according to claim 1, wherein the heater incorporates a heater resistor (52) applied to the back side of the thin insulating layer (3) in the at least one sensing area.

10. A device according to claim 1, wherein the gas-sensitive layer (18) incorporates part of a chemoresistor sensor (16, 82).

11. A device according to claim 1, wherein the at least one sensing area incorporates temperature sensing means.

12. A device according to claim 11, wherein the temperature sensing means comprises at least one bipolar transistor.

13. A device according to claim 1, wherein the material of the substrate (2) has been removed in at least one sensing area by back etching.

14. A device according to claim 1, wherein the thin insulating layer (3) is of silicon oxide and the thin semiconductor layer (4) is of silicon.

15. A device according to claim 1, wherein the at least one sensing area is integrated with at least one electronic circuit area incorporating associated circuitry (22, 24).

16. A device according to claim 1, wherein said MOSFET is a fully depleted MOSFET in the thin semiconductor layer (4) laterally isolated by LOCOS oxidation.

17. A device according to claim 1, wherein the sensing area incorporates more than one said MOSFET formed in the thin semiconductor layer (4), the MOSFET's forming a heater (73, 83) and a sensor (72, 82) adjacent one another in the thin semiconductor layer (4).

18. A device according to claim 2, wherein the gas-sensitive layer (18, 43) is incorporated in the gate of said MOSFET so that the threshold of the MOSFET changes in response to gas reaction with the gas-sensitive layer.

19. A device according to claim 16, wherein the gate comprises a conductive polymer layer which acts as the gas-sensitive layer.

20. A device according to claim 2, wherein the at least one sensing area incorporates temperature sensing means.

* * * * *